United States Patent [19]

Hinnenkamp et al.

[11] 4,299,758
[45] Nov. 10, 1981

[54] HALOGENATED CYCLOPENTADIENE DIADDUCTS OF DIACETYLENIC COMPOUNDS

[75] Inventors: James A. Hinnenkamp; Jack Kwiatek, both of Cincinnati, Ohio

[73] Assignee: National Distillers and Chemical Corp., New York, N.Y.

[21] Appl. No.: 863,185

[22] Filed: Dec. 22, 1977

[51] Int. Cl.³ .................. C07C 23/24; C08K 5/02; C08K 5/06
[52] U.S. Cl. .................. 260/45.7 R; 260/45.75 B; 570/130; 570/187
[58] Field of Search .................. 260/45.7 RL, 648 C

[56] References Cited

U.S. PATENT DOCUMENTS

| | | | |
|---|---|---|---|
| 2,813,915 | 11/1957 | Howald et al. | 260/648 C |
| 2,951,098 | 8/1960 | Hoch et al. | 260/648 C |
| 2,952,712 | 9/1960 | Roberts et al. | 260/45.7 RL |
| 2,967,842 | 1/1961 | Roberts | 260/45.7 RL |
| 3,062,898 | 11/1962 | Hoch | 260/45.7RL |
| 3,205,274 | 9/1965 | Mark | 260/648 C |
| 3,403,036 | 9/1968 | Hindersinn et al. | 260/45.7 RL |
| 3,489,715 | 1/1970 | Bierwirth et al. | 260/45.7 RL |
| 3,519,597 | 7/1970 | Weil et al. | 260/45.7 RL |
| 3,792,116 | 2/1974 | Cardenas et al. | 260/45.7 RL |
| 3,809,725 | 5/1974 | Davenport | 260/45.7 RL |

OTHER PUBLICATIONS

McBee et al., J.A.C.S., vol. 77, 1955, pp. 6674 and 6675.
Ungnade et al., Chemical Reviews, vol. 58, 1958, pp. 254–258.
Dictionary of Organic Compounds, 4th Edition, 1965, p. 1596.

*Primary Examiner*—Hosea E. Taylor
*Assistant Examiner*—R. A. White
*Attorney, Agent, or Firm*—Kenneth D. Tremain

[57] ABSTRACT

Halogenated compounds of the formula

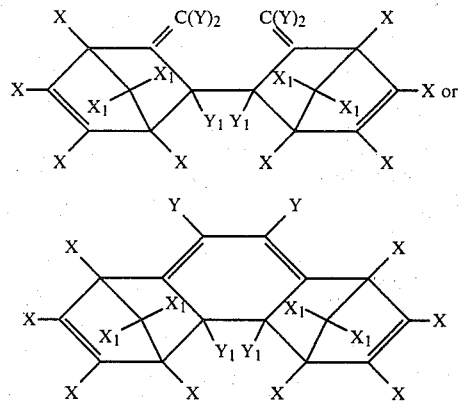

wherein each X is independently selected from the group consisting of hydrogen, chlorine, bromine and fluorine, each $X_1$ is independently selected from the group consisting of hydrogen, chlorine, bromine, fluorine and alkyl or alkoxy of 1 to 10 carbon atoms and halogen-substituted alkyl or alkoxy of 1 to 10 carbon atoms and each Y and $Y_1$ is independently selected from the group consisting of hydrogen, chlorine, bromine, fluorine, aryl, alkyl or alkoxy of 1 to 10 carbon atoms and halogen-substituted alkyl or alkoxy of 1 to 10 carbon atoms, and a process for preparing these compounds are provided. These compounds are useful as flame retardant additives for various polymers.

7 Claims, No Drawings

HALOGENATED CYCLOPENTADIENE DIADDUCTS OF DIACETYLENIC COMPOUNDS

BACKGROUND OF THE INVENTION

This invention relates to halogenated compounds of the formula

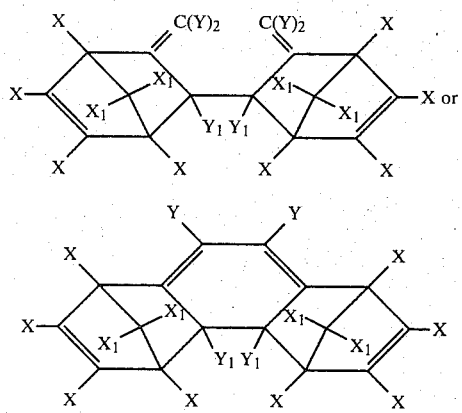

wherein each X is independently selected from the group consisting of hydrogen, chlorine, bromine and fluorine, each $X_1$ is independently selected from the group consisting of hydrogen, chlorine, bromine, fluorine and alkyl or alkoxy of 1 to 10 carbon atoms and halogen-substituted alkyl or alkoxy of 1 to 10 carbon atoms and each Y and $Y_1$ is independently selected from the group consisting of hydrogen, chlorine, bromine, fluorine, aryl, alkyl or alkoxy of 1 to 10 carbon atoms and halogen-substituted alkyl or alkoxy of 1 to 10 carbon atoms. These compounds are useful as flame retardant additives for various polymers.

There has been considerable interest in flame retardant materials. Historically, references on fire-retardant studies date back at least 200 years and were initially directed to textiles. Fire retardants for wood have also been studied extensively over the years. In recent years an area of particular interest is flame resistant polymeric compositions. In general, concern over flammable substrates has resulted in both present and potential legislation requiring that such substrates meet certain flammability standards. As a result, considerable research effort has been directed toward making flammable products flame retardant.

An important part of this research effort has been directed toward the discovery of new compounds that will impart the necessary flame retardancy to the substrate and at the same time leave the desirable properties of the substrate essentially the same. The compounds of the invention are results of such a search.

The closest work to the present invention appears to be that of Yarosh et al. shown in Chemical Abstracts Volume No. 82, Page No. 156437b whereat the synthesis and some reactions of ethynylorganosiloxanes is shown. The reaction of a diacetylenic silicone compound with hexachlorocyclopentadiene provided an ethynylorganosiloxane, which is substantially different in structure from the compounds of the present invention.

SUMMARY OF THE INVENTION

New compounds of the formula

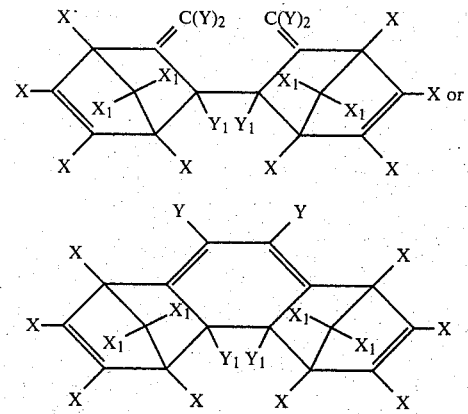

have been discovered. These compounds are useful as flame retardants for flammable substrates, such as polymers.

DESCRIPTION OF THE PREFERRED EMBODIMENTS

In general, any flammable substrate material may be rendered flame retardant by incorporation therewith of the above-identified flame-retardant compounds. As used in this disclosure, the term "flame retardant" is intended to refer to that particular property of a material which provides it with a degree of resistance to ignition and burning. This property may be conveniently evaluated by means of any of the standard flame retardancy tests, such as the Limiting Oxygen Index test which is more fully described hereinbelow in the Examples. Examples of flammable substrates which may be rendered flame retardant and methods of providing flame retardancy thereto using flame retardant additives such as the compounds of the invention are shown in "The Chemistry and Uses of Fire Retardants" by John W. Lyons, John Wiley & Sons, Inc., 1970, "Flame Retardancy of Polymeric Materials", Volumes 1 and 2, edited by W. C. Kuryla and A. J. Papa, Marcel Dekker, Inc., 1973 and "Fire Resistance and Flame Retardant Polymers", by Maurice W. Ranney, Noyes Data Corp., 1974, said publications being incorporated herein by reference.

Exemplary flammable substrates include wood, paper, textiles, fibers, rubbers, waxes, resins (polymers), e.g., polyolefins, such as polyethylene and polypropylene, and copolymers thereof, polyvinyl halide, polystyrene, polyesters, polyurethanes, polyamides (nylons), polyhydrocarbons, copolymers of ethylene and vinyl acetate, containing, for example, up to about 95%, or more, by weight ethylene, terpolymers, such as acrylonitrile-butadiene-styrene, and the like.

The flame retardant amount of the compound of the invention which is added to the substrate material to impart flame retardancy thereto varies widely depending on the particular effect desired and generally will be in a range of about 0.5% to 60% by weight of the material.

The compounds can be incorporated into the materials, e.g., resins, by any known method. That is to say, the flame-retardant additive may be added to the resin by milling the resin and the compound on, for example, a two-roll mill, in a Banbury mixer, etc., or the compound may be added by molding it and the resin simultaneously, extruding the compound and resin or by merely blending the resin in powder form with the compound and thereafter forming the final desired article. Additionally, the compound may also be added during the resin manufacture, i.e., during the polymerization procedure by which the resin is made, provided the catalyst, etc., and other ingredients of the polymerization system are inert thereto. An important feature of the invention is the production of thermoplastic and thermoset resin compositions which are flame retardant, i.e., have high resistance to heat, since these are of considerable commercial importance. For example, such articles as castings, moldings, foamed or laminated structures and the like are required, or at least desired, to be resistant to fire and flame and to possess the ability to endure heat without deterioration. Typical illustrations of such applications can be found in wire and cable coverings and castings for live electrical contacts which should not be ignited or deteriorated by heat and sparks. Structural members such as pipes, wall coverings, wall paneling, windows and items such as ash trays, waste baskets, fibers, textiles and the like are further examples of products wherein flame retardance is desirable.

It is also within the scope of the instant invention to incorporate such ingredients as plasticizers, dyes, pigments, heat and light stabilizers, antioxidants, antistatic agents, photochromic materials and the like into the flame-retarded compositions claimed herein. The improved fire retardancy of the normally combustible polymers can be improved, if desired, by incorporating metallic compounds such as compounds of arsenic, antimony or bismuth in the polymer composition. Antimony oxide is the antimony compound that is presently preferred for use in the present invention. However, many antimony compounds are suitable. U.S. Pat. No. 2,996,528 discloses suitable antimony salts or organic acids and their pentavalent derivatives.

The new compounds may be any of those delineated by the general formula

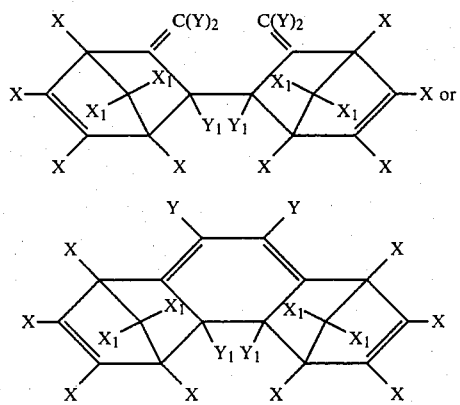

wherein each X is independently selected from the group consisting of hydrogen, chlorine, bromine and fluorine, each $X_1$ is independently selected from the group consisting of hydrogen, chlorine, bromine, fluorine and alkyl or alkoxy of 1 to 10 carbon atoms and halogen-substituted alkyl or alkoxy of 1 to 10 carbon atoms and each Y and $Y_1$ is independently selected from the group consisting of hydrogen, chlorine, bromine, fluorine, aryl, alkyl or alkoxy of 1 to 10 carbon atoms and halogen-substituted alkyl or alkoxy of 1 to 10 carbon atoms.

Of particular interest in the invention are those compounds which contain at least one halogen atom, and preferably more than about 8, e.g., wherein the X, $X_1$, Y and $Y_1$ atoms are predominately halogen, especially chlorine or bromine, because of the higher percentage of halogen in the compound. Also preferred are those wherein each X and $X_1$ is chlorine or bromine and each Y and $Y_1$ is hydrogen because of the demonstrated ability as flame retardants. Specific examples of these compounds will include 5,5'-Bi-(1,2,3,4,7,7-Hexachloro-6-Methylene-Bicyclo-[2.2.1]-hept-2-enyl); 5,5'-Bi-(1,2,3,4,7,7-Hexachloro-6-Dichloromethylene-Bicyclo-[2.2.1]-hept-2-enyl); 5,5'-Diphenyl-5,5'-Bi-(1,2,3,4,7,7-Hexachloro-6-Methylene-Bicyclo-[2.2.1]-hept-2-enyl); 5,5'-Bi-(1,2,3,4-Tetrachloro-7,7'-Dimethoxy-6-Methylene-Bicyclo-[2.2.1]-hept-2-enyl); 5,5'-Bi-(1,2,3,4,7,7-Hexabromo-6-Methylene-Bicyclo-[2.2.1]-hept-2-enyl); 5,5'-Bi-(1,4 dibromo-2,3,7,7-tetrachloro-6-Methylene-Bicyclo-[2.2.1]-hept-2-enyl); 1,2,3,4,5,6,7,8,11,11,12,12-dodecachloro-1,4,4a,4b,5,8-hexahydro-1,4:5,8-dimethanophenanthrene; 1,2,3,4,5,6,7,8,9,10,11,11,12,12-tetradecachloro-1,4,4a,4b,5,8-hexahydro-1,4:5,8-dimethanophenanthrene.

An important feature of the invention is a process for making the compounds. The process comprises reacting at an elevated temperature a cyclopentadiene of the formula

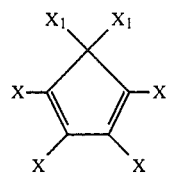

and a 1,5-hexadiyne of the formula

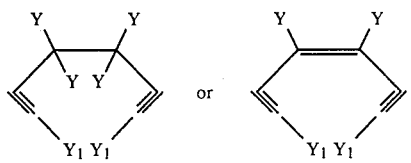

wherein each X, $X_1$, Y and $Y_1$ is as defined hereinabove. A preferred cyclopentadiene embodiment is hexachlorocyclopentadiene and a preferred diyne is 1,5-hexadiyne. Some of the halogenated cyclopentadienes that may be employed are as follows: hexahalocyclopentadienes such as hexachlorocyclopentadiene, hexafluorocyclopentadiene, hexabromocyclopentadiene, pentachloromonobromocyclopentadiene, tetrachlorodibromocyclopentadiene, etc.; pentahalomonoalkylcyclopentadienes, such as pentachloromethylcyclopentadiene, pentabromomethylcyclopentadiene, tetrahalodialkylcyclopentadienes, such as tetrachlorodimethylcyclopentadiene, tetrabromodimethylcyclopentadiene; some of the alkoxy cyclopentadienes that may be employed are pentahaloalkoxycyclopentadienes such as pentachloromethoxycyclopentadiene and pentabromoethoxycyclopentadiene; tetrahalodialkoxycyclopentadienes such as tetrachlorodimethoxy, tetrachlorodiethoxy, tetrachlorodipropoxy, tetrachlorodibutoxy, tetrachlorodipentoxy or tetrachlorodihexoxycyclopentadiene.

Some of the halogen-substituted alkyl cyclopentadienes are:

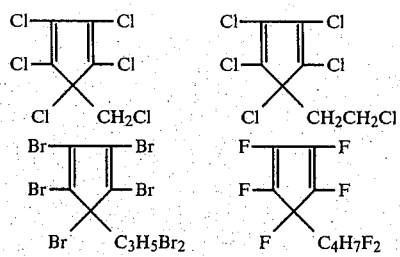

Some of the halogen substituted alkoxy cyclopentadienes are:

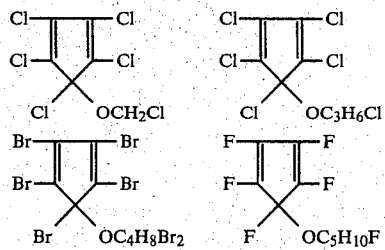

Some of the hexadiyne compounds that may be employed are: 1,5-hexadiyne; 2,6-octadiyne; 3,3,4,4-tetrachloro-hexa-1,5-diyne; 3,4-diphenyl-hexa-1,5 diyne; 3 hexene-1,5-diyne; 1,6 diphenyl-hexa-1,5-diyne; 3,4-di(-chloromethyl)-hexa-1,5-diyne; 3,4-dimethyl-hexa-1,5 diyne.

Although the reaction temperature may vary over a wide range, an elevated temperature above about 60° C., e.g., 90° C., is generally employed with a preferred range being about 130° to 160° C. The proportions of reactants are preferably at least the stoichiometric amount of two moles of cyclopentadiene to one mole of hexadiyne, although greater or lesser amounts may be employed. A preferred process comprises maintaining the cyclopentadiene material in a heated condition with stirring under a nitrogen blanket. The hexadiyne material is added intermittently over a period of hours, e.g., 10-20 hours with refluxing. After the addition is complete, refluxing is continued for an additional period of time, e.g., about 12-36 hours. Upon cooling, the addition of hexane causes the precipitation of the compound of the invention, which may be collected by vacuum filtration and washed with hexane and recovered. Other similar processes may suitably be employed.

Various embodiments of the present invention will now be illustrated by reference to the following specific examples. It is to be understood, however, that such examples are presented for purposes of illustration only, and the present invention is in no way to be deemed as limited thereby. All parts and percentages given are by weight and temperatures in degrees Centigrade unless otherwise indicated.

EXAMPLE 1

Preparation of 5,5'-Bi-(1,2,3,4,7,7-Hexachloro-6-Methylene Bicyclo[2.2.1]hept-2-enyl)

35.0 g. (0.13 mole) of hexachlorocyclopentadiene in a 100 ml. round bottom flask containing an addition funnel and water condenser, was heated to 145° C. with stirring under a nitrogen blanket. 1,5-hexadiyne, 5.0 g. (0.064 mole), was added intermittently over 16 hours. After the addition was complete, the mixture was refluxed another 26 hours. Upon cooling, a viscous dark brown oil separated, and the addition of hexane caused the precipitation of a tan solid. The solid was collected by vacuum filtration and washed thoroughly with hexane. After drying in air, the solid was recrystallized from benzene to give a white solid having a melting point of about 231°-232° C. A yield of 14% was obtained.

Elemental analysis and $^{13}C$ nuclear magnetic resonance spectroscopy (NMR) of the product confirms the following structure wherein each X and $X_1$=Cl and each Y and $Y_1$=H:

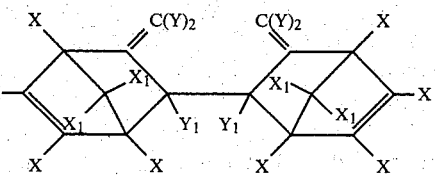

Elemental Analysis

|  | Carbon | Hydrogen | Chlorine |
|---|---|---|---|
| Calc. (%) | 30.81 | 0.97 | 68.21 |
| Found (%) | 30.83 | 1.02 | 68.13 |

EXAMPLE 2

Example 1 was repeated except that the reaction temperature was 90° C. and the total reaction time was 115 hours. The same product was formed.

EXAMPLE 3

Example 1 was repeated except that the reaction temperature was ambient and the total reaction time was 30 days. No product was formed.

Any appropriate flame-retardance test may be used to determine the flame-retardant properties of the flame-retarded compositions of the instant invention. One test is to determine its limiting oxygen index (LOI) by means of ASTM D-2863-70. In brief, this procedure directly relates flame retardancy to a measurement of the minimum percentage concentration of oxygen in an oxygen:nitrogen mixture which permits the sample to burn; the LOI being calculated as follows:

$$LOI = \frac{[O_2]}{[O_2] + [N_2]} \times 100$$

Thus, a higher LOI is indicative of a higher degree of flame retardancy.

EXAMPLE 4

Use as a flame retardant

On a Bollins two-roll mill the compositions shown in Table 1 were compounded by blending for about 30 minutes at about 110° C. The blended material was then molded into a plaque 76×152×2 millimeters (mms.), cured at 200° C. for 5 minutes and tested according to ASTM D-2863-70. A typical LOI value for the resin without a flame retardant is about 18.

TABLE 1

| | Compositions (parts by weight) | | | |
|---|---|---|---|---|
| Resin[1] | 100 | 100 | 100 | 100 |
| Product of Example 1 | 43.75 | 57.00 | — | — |
| Dechlorane[2] | — | — | 43.75 | 57.00 |
| Agerite Resin D[3] | 1.67 | 1.67 | 1.67 | 1.67 |
| $Sb_2O_3$ | 14.58 | 19.00 | 14.58 | 19.00 |
| Dicup 40 KE[4] | 5.00 | 5.00 | 5.00 | 5.00 |
| LOI | 25.8 | 27.7 | 27.0 | 27.4 |

[1]The resin is a copolymer of ethylene and vinyl acetate containing about 91% ethylene and 9% vinyl acetate.

[2]Dechlorane 602 is a commercial flame retardant additive purchased from Hooker Chemical Co. and is 1, 2, 3, 4, 6, 7, 8, 9, 10, 10, 11, 11 - dodecachloro - 1, 4, 4a, 5a, 6, 9, 9a, 9b - octahydro - 1, 4, 6, 9 - dimethanodibenzofuran.

[3]Agerite Resin D is a polymerized 1,2-dihydro-2,2,4-trimethylquinoline.

[4]Dicup 40 KE is dicumyl peroxide.

The above data illustrates the improved flame retardancy developed in the polyblends containing the novel compounds of the invention.

EXAMPLE 5

Preparation of 1,2,3,4,5,6,7,8,11,11,12,12-dodecachloro-1,4,4a,4b,5,8-hexahydro-1,4:5,8-dimethanophenanthrene.

One mole of 3-hexene-1,5 diyne is reacted with 2 moles of hexachlorocyclopentadiene following the procedure EXAMPLE 1.

It will be apparent that many changes and modifications of the several features described herein may be made without departing from the spirit and scope of the invention. It is therefore apparent that the foregoing description is by way of illustration of the invention rather than limitation of the invention.

We claim:

1. A compound of the formula

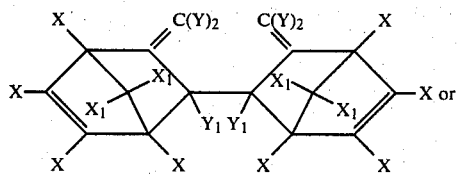

or

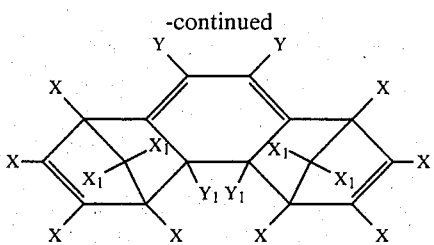

wherein each X is independently selected from the group consisting of hydrogen, chlorine, bromine and fluorine, each $X_1$ is independently selected from the group consisting of hydrogen, chlorine, bromine, fluorine, and alkyl or alkoxy of 1 to 10 carbon atoms and halogen-substituted alkyl or alkoxy of 1 to 10 carbon atoms and each Y and $Y_1$ is independently selected from the group consisting of hydrogen, chlorine, bromine, fluorine, aryl, alkyl or alkoxy of 1 to 10 carbon atoms and halogen-substituted alkyl or alkoxy of 1 to 10 carbon atoms.

2. A compound of claim 1 wherein each X and $X_1$ is chlorine and each Y and $Y_1$ is hydrogen.

3. A process for making a compound of the formula of claim 1 which comprises reacting at an elevated temperature a cyclopentadiene of the formula

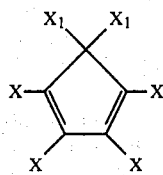

and a 1,5-hexadiyne of the formula

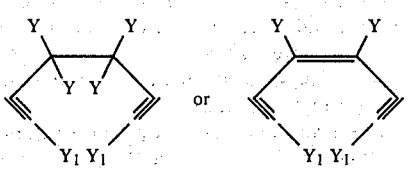

4. The process of claim 3 wherein the cyclopentadiene is hexachlorocyclopentadiene, the hexadiyne is 1,5-hexadiyne and the reaction temperature is in the range of about 130° to 160° C.

5. The process of claim 3 wherein the hexadiyne is 3-hexene-1,5 diyne.

6. A flame retardant polymeric composition comprising a polymer and a flame retardant amount of the compound of claim 1.

7. The flame retardant composition of claim 6 wherein the compound is the compound of claim 2.

* * * * *